United States Patent [19]

Muller et al.

[11] 4,372,822

[45] Feb. 8, 1983

[54] PRODUCTION OF ANHYDROUS ETHANOL

[75] Inventors: Werner C. Muller, Dobbs Ferry, N.Y.; Franklyn D. Miller, Cincinnati, Ohio

[73] Assignee: National Distillers & Chemical Corp.

[21] Appl. No.: 287,018

[22] Filed: Jul. 27, 1981

Related U.S. Application Data

[63] Continuation of Ser. No. 156,979, Jun. 6, 1980, abandoned.

[51] Int. Cl.[3] .............................................. B01D 3/36
[52] U.S. Cl. ........................................ 203/19; 203/23; 203/25; 203/27; 203/68; 203/69; 203/75; 203/77; 203/78; 203/DIG. 13
[58] Field of Search .............. 568/913; 203/19, 21–23, 203/25, 27, 68, 69, 71, 73–75, 78, 77, DIG. 13

[56] References Cited

U.S. PATENT DOCUMENTS 3,445,345  5/1969  Katzen et al. .......................... 203/25
4,161,429  7/1979  Baiel et al. ............................ 203/18

Primary Examiner—Frank Sever
Attorney, Agent, or Firm—Kenneth D. Tremain

[57] ABSTRACT

Substantially anhydrous, i.e., absolute, ethanol is distilled at high thermal efficiency from a dilute feedstock such as a fermentate ("beer") containing one or more low boiling components whose removal at least in part prior to anhydrous distillation is necessary in order to achieve an acceptable degree of phase separation in a decanter. Most of the low boiling component(s) are removed from the feed in a rectifying column with the balance of the low boiling component(s), insufficient in amount to seriously interfere with proper operation of the decanter, being removed from the system employing a light-ends column. Both the anhydrous column and the light-ends column are operated at substantially superatmospheric pressure with thermal values recovered from these columns being used in the operation of the rectifying column.

9 Claims, 1 Drawing Figure

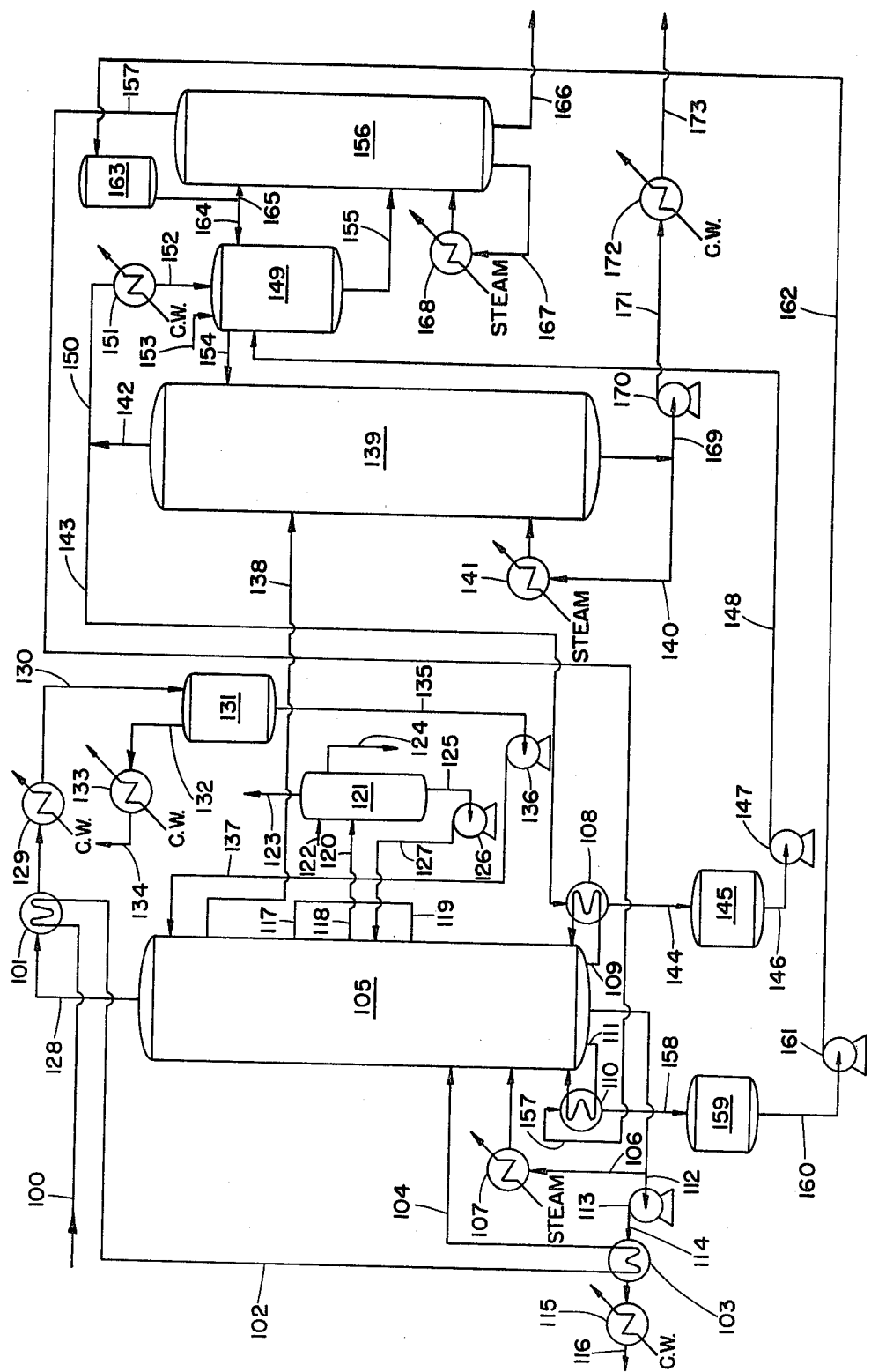

PRODUCTION OF ANHYDROUS ETHANOL

This is a continuation of application Ser. No. 156,979, filed June 6, 1980, now abandoned.

CROSS REFERENCE TO RELATED APPLICATION

This application is related to commonly assigned, copending U.S. Pat. No. 043,189, filed May 29, 1979 entitled "Production of Anhydrous Ethanol".

BACKGROUND OF THE INVENTION

1. Field of the Invention

This invention relates to the field of processes of distillation and, more particularly, to processes for the recovery by distillation of anhydrous ethanol from a dilute aqueous feedstock.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline—10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter, the chemical and/or enzymatic hydrolysis of starch to fermentable sugar (liquefaction and saccharification), the fermentation of sugar to provide a dilute solution of ethanol ("beer") and the recovery of anhydrous or concentrated ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy as possible so as to maximize the energy return for the amount of ethanol produced and enhance the standing of the ethanol as an economically viable replacement for petroleum based raw materials.

To date, however, relatively little concern has been given to the energy requirements for manufacturing ethanol, especially with regard to the ultimate distillation operation which is the most energy intensive procedure in the ethanol production sequence whether the ethanol be derived from a petroleum or vegetative source.

The substitution of alcohol for at least a portion of petroleum based fuels is particularly critical for developing economies where proven domestic petroleum reserves are limited, such as in India and Brazil and these nations have therefore increasingly emphasized the production of alcohol from vegetative sources. The most common subject operation employs cane sugar in a fermentation-distillation operation which conveniently utilizes the bagasse by-product as a fuel source.

Processes for the azeotropic distillation of a dilute ethanol feed to provide absolute alcohol are well known (viz., U.S. Pat. Nos. 1,583,314; 1,486,717; 1,586,732; 1,670,053; 1,761,779; 1,763,722; 1,830,469; 1,873,005; 1,935,529; 2,050,513; 2,386,058; 2,640,017; 2,695,867; 3,404,186; and 3,960,672). In a typical anhydrous distillation process, a concentrated ethanol stream is combined with benzene (or other azeotrope-forming liquid), and the mixture is heated in a distillation column to provide a ternary vapor mixture containing ethanol, benzene and water at the top of the column, a binary mixture of ethanol and benzene in the middle of the column and absolute ethanol at the bottom of the column. Part of the vapors at the head of the column are condensed and the condensate is returned to the top of the distillation column as reflux. The remaining part of the vapors are condensed and separated in a decanter or like apparatus into a benzene-rich upper layer which is returned to the distillation column and an aqueous ethanol-rich lower layer from which residual benzene is removed and recycled. When the source of ethanol for this and similar anhydrous distillation processes contains one or more low boiling compounds such as ethyl acetate in amounts which would tend to interfere with good separation of the benzene-rich and aqueous ethanol-rich layers in the decanter, it is necessary that such compounds be removed from the feed prior to anhydrous distillation. Commonly assigned, copending U.S. patent application Ser. No. 043,189, filed May 29, 1979, describes a method for the anhydrous distillation of a dilute aqueous ethanol feed in which low boiling components are removed from the feed in a heads stripping column prior to concentration of the ethanol in a rectifying column. Desirable as this procedure may be, the operation of the heads stripping column in application Ser. No. 043,189 accounts for a significant amount of the overall energy requirements of the system.

SUMMARY OF THE INVENTION

In accordance with this invention a process is provided for obtaining substantially anhydrous ethanol which comprises: concentrating to high proof a dilute aqueous ethanol feed containing one or more dissolved low boiling components in an amount which would, unless removed therefrom, tend to interfere with phase separation in a decanter, to provide an overhead vapor stream containing a major proportion of the low boiling component(s) present in the feed, and a pasteurized cut of concentrated aqueous ethanol containing the balance of the low boiling component(s) present in the feed; dehydrating the aforesaid pasteurized cut to substantially complete dryness in an anhydrous column operated under substantially elevated pressure with thermal values recovered therefrom being used in the operation of the rectifying column; separating condensed overhead vapors from the anhydrous column in a decanter into an azeotrope-rich phase and a water-rich phase containing ethanol and low boiling component(s); and, separating the water-rich phase obtained from the decanter into vapor overheads containing ethanol and low boiling component(s), and water, in a light-ends column operated under substantially elevated pressure with thermal values recovered therefrom being used in the operation of the rectifying column.

By eliminating the separation of low boiling component(s) in a separate heads stripping column as described in commonly assigned, copending U.S. patent application Ser. No. 043,189, filed May 29, 1979, the anhydrous distillation process of this invention achieves a significant reduction in the overall energy requirements of the system.

The anhydrous distillation process herein is applicable to any dilute aqueous ethanol feedstock such as "beer" obtained from fermentation (up to about 12 weight percent ethanol) containing one or more low boiling components such as ethyl acetate, biacetyl, acetaldehyde, acrolein, methanol, diethyl acetal, and so forth, in amounts which would tend to interfere with proper management of the process. In addition, the feed may also contain such high boiling impurities as fusel oil and polymeric oils which should be removed from the rectifying column to avoid being accumulated therein.

BRIEF DESCRIPTION OF THE DRAWING

The accompanying drawing is a diagrammatic flow sheet of a preferred embodiment of the process of the invention.

DESCRIPTION OF THE PREFERRED EMBODIMENTS

Referring to the drawing, a dilute impure aqueous ethanol feed obtained from the fermentation of sugar ("beer") containing from about 5 to 12 weight percent ethanol and minor amounts one or more low boiling components such as ethyl acetate and optionally, high boiling impurities such as fusel oil and possibly other impurities, is conveyed through line 100 to and through beer preheater 101 which transfers thermal values recovered from the overhead vapor passing from rectifying column 105 to the beer. The partially preheated beer continues through line 102 to and through beer preheater 103 where the beer picks up additional thermal values recovered from the still bottoms passing from rectifying column 105. Emerging from beer preheater 103, the beer, now heated to its atmospheric boiling point of about 210° F., passes through line 104 to rectifying column 105 wherein the ethanol is concentrated to high proof and preferably to at least about 95 volume percent (190° proof). Rectifying column 105 is operated at or about atmospheric pressure and to the extent necessary, can be provided with heat supplied to liquid recirculating through line 106 passing through reboiler 107 supplied with steam. By operating anhydrous column 139 and light-ends column 156 at significantly elevated levels of pressure, a sufficient amount of heat is recoverable from each of these columns to supply a good part, if not all, of the thermal operating requirements of rectifying column 105.

Thus, heat contained in that portion of the vapor overheads passing from anhydrous column 139 through lines 142 and 143 is transferred through reboiler shell 108 to rectifying column bottoms recirculating through line 109. Similarly, heat contained in the vapor overheads passing from light-ends column 156 through line 157 is transferred through reboiler shell 110 to rectifying column bottoms recirculating through line 111. Hot still bottoms passing through line 112 are conveyed by pump 113 through line 114 to beer preheater 103 giving up a portion of their heat to the incoming beer feed. The still bottoms are then cooled by heat exchanger 115 and are discharged through line 116. Advantageously, the still bottoms, which contain soluble proteins and amino acids contained in the original feed, are recovered for use as fertilizer, animal feed or to help satisfy the nutritive requirements of yeast in an ethanol fermentation system. Sidestreams containing fusel oil are taken at different levels of rectifying column 105 through lines 117, 118 and 119 and are conveyed through common line 120 to separator vessel 121 supplied with wash water through line 122. Vapor overhead in separator vessel 121 is discharged therefrom through line 123 with the fusel oil being recovered through line 124. The fusel oil can be burned as fuel or added to the product anhydrous alcohol if the nature of the use of the latter permits. The aqueous ethanol effluent passing from separator vessel 121 through line 125 is moved by pump 126 through line 127 and into rectifying column 105. The overhead vapor from rectifying column 105 passes through line 128 to and through preheater 101 giving up a portion of its heat to the incoming beer feed and the vapor thereafter passes through condenser 129 with the aqueous ethanol condensate entering rectifying column reflux drum 131 through line 130. Vapor overheads from reflux drum 131 are passed through line 132 to condenser 133 with acetaldehyde being discharged from the system through line 134. The aqueous ethanol passing from reflux drum 131 through line 135 is driven by pump 136 through line 137 to the top of rectifying column 105 to serves as reflux. A pasteurized cut of concentrated aqueous ethanol withdrawn from rectifying column 105 is conveyed through line 138 to anhydrous column 139 which is run at substantially superatmospheric pressure, preferably within the range of from about 60 to about 150 psig, and more preferably from about 80 to about 130 psig. Heat is supplied to anhydrous column 139 by recirculating liquid in line 140 through reboiler 141 supplied with steam. Part of the vapor overhead (azeotrope-forming agent, ethanol, residual low boiling component(s) and water) passing from anhydrous column 139 through line 142 is conveyed through line 143 giving up heat in reboiler shell 108 to rectifying column liquid recirculating through line 109. The condensed liquid resulting from the passage of anhydrous column overheads through reboiler shell 108 enters drum 145 through line 144 and passing therefrom through line 146 is conveyed by pump 147 through line 148 to the top of decanter 149. Another part of the vapor passing from anhydrous column 139 through line 142 is conveyed through line 150 to and through condenser 151 with the condensate entering decanter 149 through line 152. Start-up azeotrope-forming agent can be suppllied to the system at any convenient point such as through line 153 to decanter 149. The upper phase in decanter 149 which is rich in azeotrope-forming agent is conveyed through line 154 to the top of anhydrous column 139 to provide reflux liquid. The lower water-rich phase in decanter 149 containing ethanol and low boiling component(s) passes through line 155 to light-ends column 156 which is operated at superatmospheric pressure under the same or similar conditions used in the operation of anhydrous column 139. Vapor overheads from light-ends column 156 are conveyed through line 157 giving up heat in reboiler shell 110 to rectifying column liquid recirculating through line 111. The condensed liquid resulting from the passage of light-ends column overheads through reboiler shell 110 enters drum 159 through line 158 and passing therefrom through line 160 is conveyed by pump 161 through line 162 to the top of reflux drum 163. Reflux liquid from reflux drum 163 enters the top of the decanter 149 through line 164 and the top of light-ends column 156 through line 165. The bottoms from light-ends column 156, consisting of clean water, are discharged through line 166 and may be discarded or recycled to process as desired. Heat for the operation of the light-ends column is supplied thereto by recirculating liquid in line 167 through reboiler 168 supplied with steam. Substantially anhydrous ethanol is recovered from the bottom of anhydrous column 139 through line 169 and is conveyed by pump 170 through line 171 past cooler 172 and thereafter to storage through line 173. While any of the azeotrope-forming agents heretofore employed for the anhydrous distillation of ethanol, e.g., benzene, toluene, etc., can be used herein with good results, it is preferred to employ cyclohexane for this purpose especially when anhydrous column 150 is operated under pressure. In the past, it has been proposed to carry out anhydrous distillation of ethanol at elevated pressure employing diethyl ether as an entraining agent. (Moeller et al., *Industrial Engineering Chemistry*, Vol. 43. No. 3, pp 711–717 (1951); Wentworth et al., *Trans. Am. Inst. Chem. Engrs.*, Vol. 39, pp. 565–578 (1943) and Vol. 36, pp 785–799 (1940)). However diethyl ether has numerous drawbacks compared to cyclohexane for this purpose. For one thing, much higher anhydrous column operating pressures would be required in order to provide sufficient heat to run a rectifying column when working with diethyl ether. For another, diethyl ether is more hazardous than cyclohexane and reasons of safety alone militate against its use. Moreover, ether gives inferior separation between ethanol and water compared to that provided by cyclohexane.

What is claimed is:

1. A process for obtaining substantially anhydrous ethanol which comprises:

(a) concentrating to high proof a dilute aqueous ethanol feed containing one or more dissolved components in an amount which would, unless removed therefrom, tend to interfere with phase separation in a decanter, to provide an overhead vapor stream containing a major proportion of the low boiling component(s) present in the feed, and a pasteurized cut of concentrated ethanol containing the balance of the low boiling component(s) present in the feed of sufficient value to eliminate the requirement of a preliminary extractive distillation step;

(b) dehydrating the aforesaid pasteurized cut to substantially complete dryness in an anhydrous column operated under substantially elevated pressure with thermal values recovered therefrom being used in the operation of the rectifying column;

(c) separating condensed overhead vapors from the anhydrous column in a decanter into an azeotrope-rich phase and a water-rich phase containing ethanol and substantially all of said balance of said low boiling component(s); and, (d) separating the water-rich phase obtained from the decanter into vapor overheads containing ethanol and low boiling component(s), and water, in a light-ends column operated under substantially elevated pressure with thermal values recovered therefrom being used in the operation of the rectifying column.

2. The process of claim 1 wherein the anhydrous column is operated at from about 60 to about 150 psig pressure.

3. The process of claim 2 wherein the anhydrous column is operated at from about 80 to about 130 psig pressure.

4. The process of claim 1 wherein the light ends column is operated at from about 60 to about 150 psig pressure.

5. The process of claim 4 wherein the light ends column is operated at from about 80 to about 130 psig pressure.

6. The process of claim 1, wherein prior to introduction into the rectifying column, the dilute ethanol feed is preheated with thermal values recovered from the rectifying column overhead vapor and/or bottoms.

7. The process of claim 1 wherein the azeotrope-forming agent is benzene.

8. The process of claim 1 wherein the azeotrope-forming agent is cyclohexane.

9. The process of claim 1 wherein the ethanol feed contains high boiling impurities which are removed therefrom as a liquid sidestream taken from the rectifying column.

* * * * *